(12) United States Patent
Evers et al.

(10) Patent No.: US 9,834,527 B2
(45) Date of Patent: Dec. 5, 2017

(54) MACROCYCLIC UREA DERIVATIVES AS INHIBITORS OF TAFIA, THEIR PREPARATION AND THEIR USE AS PHARMACEUTICALS

(71) Applicant: SANOFI, Paris (FR)

(72) Inventors: Andreas Evers, Frankfurt am Main (DE); Christopher Kallus, Frankfurt am Main (DE); Michael Wagner, Frankfurt am Main (DE); Hermut Wehlan, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/895,695

(22) PCT Filed: Jun. 5, 2014

(86) PCT No.: PCT/EP2014/061669
§ 371 (c)(1),
(2) Date: Dec. 3, 2015

(87) PCT Pub. No.: WO2014/198620
PCT Pub. Date: Dec. 18, 2014

(65) Prior Publication Data
US 2016/0137618 A1 May 19, 2016

(30) Foreign Application Priority Data

Jun. 10, 2013 (EP) .................................... 13305779

(51) Int. Cl.
| C07D 413/12 | (2006.01) |
| C07D 273/01 | (2006.01) |
| A61K 31/395 | (2006.01) |
| A61K 31/4427 | (2006.01) |
| A61P 7/02 | (2006.01) |
| A61K 45/06 | (2006.01) |
| C07D 213/75 | (2006.01) |

(52) U.S. Cl.
CPC .......... C07D 273/01 (2013.01); A61K 31/395 (2013.01); A61K 31/4427 (2013.01); A61K 45/06 (2013.01); C07D 213/75 (2013.01); C07D 413/12 (2013.01)

(58) Field of Classification Search
CPC .. C07D 413/12; C07D 273/01; A61K 31/395; A61K 31/4427
USPC .................. 514/450, 338, 339; 467/467, 468
See application file for complete search history.

(56) References Cited

U.S. PATENT DOCUMENTS

| 8,580,777 B2 | 11/2013 | Kallus et al. | |
| 8,722,655 B2 | 5/2014 | Kallus et al. | |
| 9,126,955 B2 | 9/2015 | Kallus et al. | |
| 9,309,207 B2 * | 4/2016 | Kallus | .................. C07D 273/01 |
| 2011/0178130 A1 * | 7/2011 | Kallus | .................. C07D 273/01 514/338 |

FOREIGN PATENT DOCUMENTS

| EP | 0611776 A2 | 8/1994 |
| EP | 0641779 A1 | 3/1995 |
| WO | 9730080 | 8/1997 |
| WO | 9911606 | 3/1999 |
| WO | 0044335 | 8/2000 |
| WO | 0066152 | 11/2000 |
| WO | 0066557 | 11/2000 |
| WO | 0214285 | 2/2002 |
| WO | 03013526 | 2/2003 |
| WO | 03027128 | 4/2003 |
| WO | 03061652 | 7/2003 |
| WO | 03061653 | 7/2003 |
| WO | 03080631 | 10/2003 |
| WO | 03106420 | 12/2003 |
| WO | 2005105781 | 11/2005 |
| WO | 2007045339 | 4/2007 |
| WO | 2008067909 | 6/2008 |
| WO | 2009146802 | 12/2009 |

OTHER PUBLICATIONS

U.S. Official Action dated Dec. 7, 2012 in U.S. Appl. No. 12/996,460, pp. 1-7.
U.S. Official Action dated Jan. 28, 2014 in U.S. Appl. No. 14/048,339, pp. 1-6.
Aeberhard, U. "277. Structure and Chemistry of Malonylmethyl- and Succinyl-Radicals. The Search for Homolytic 1,2 Rearrangements" Helv. Chim. Acta 1983, 66, 2740-2759.
Aitken, R.A. et al., "Synthesis and Pyrolytic Behaviour of Thiazolidin-2-0ne 1, 1-Dioxides", J. Chem. Soc., Perkin Trans. 1:2139-2145 (1997).
Bajzar, L., "Thrombin Activatable Fibrinolysis Inhibitor and an Antifibrinolylic Pathway", Arteriosclerosis, Thrombosis, and Vascular Biology 20:2511-2518 (2000).
Borghese, A. et al., "Mild and Safer Preparative Method for Nonsymmetrical Sulfamides Via N-Sulfamoyloxazolidinone Derivatives: Electronic Effects Affect the Transsulfamoylation Reactivity", Organic Process Research & Development 10:770-775 (2006).
Bouma, B.N. et al., "Thrombin-Activatable Fibrinolysis Inhibitor (TAFI, Plasma Procarboxypeptidase B, Procarboxypeptidase R, Procarboxypeptiase U)", Journal of Thrombosis and Haemostatis 1:1566-1574 (2003).

(Continued)

*Primary Examiner* — Irina Neagu
(74) *Attorney, Agent, or Firm* — McDonnell Boehnen Hulbert & Berghoff LLP

(57) ABSTRACT

The present invention relates to macrocydic urea derivatives of the formula I (I) in which R1, R2, R3, V and Y are as defined below. The compounds of the formula I are inhibitors of the enzyme TAFIa (activated thrombin-activatable fibrinolysis inhibitor). The invention further relates to the process for the preparation of the compounds of formula I and to the use thereof as medicaments.

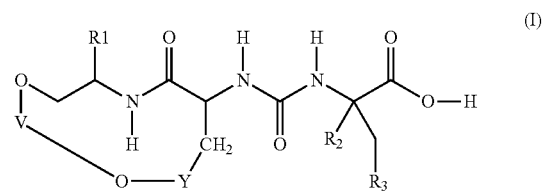

9 Claims, No Drawings

(56) References Cited

OTHER PUBLICATIONS

Carpino, L.A. et al., "Advantageous Applications of Azabenzotriazole (Triazolopyridine)-Based Coupling Reagents to Solid-Phase Peptide Synthesis", J. Chem. Soc., Chem. Commun., 1994:201-203 (1994).

Castro, B. et al., "Reactifs De Couplage Peptidique IV (1)-L'Hexaftuorophosphate De Benzotriazolyl N-Oxytrisdimethylamino Phosphonium (B.O.P.)", Tetrahedron Letters 14:1219-1222 (1975).

Connon, S.J. et al., "Recent Developments in Olefin Cross-Metathesis", Angewandte Chemie Int. Ed. 42:1900-1923 (2003).

Dolbier, Jr., W.R. et al., "Trimethylsilyl Fluorosulfonyldifluoroacetate (TFDA): A New, Highly Efficient Difluorocarbene Reagent", Journal of Fluorine Chemistry 125:459-469 (2004).

Dourtoglou, V. et al., "L-Hexafluorophosphate De O-Benzotriazolyi-N,N-Tetramethyluronium: Un Reactif De Couplage Peptidique Nouveau Et Efficace", Tetrahedron Letters 15:1269-1272 (1978).

Felix, A.M. et al., "Applications of BOP Reagent in Solid Phase Synthesis", Int. J. Peptide Protein Res. 31 :231-238 (1988).

Ho, M. et al., "A Convenient Synthesis of Chiral N-Boc-Amino Ethers as Potential Peptide Bond Surrogate Units", Tetrahedron Letters 34(41):6513-6516 (1993).

Hosub, V. "Enantioselective Synthesis of [alpha]-Quaternary Amino Acid Derivatives by Sequential Enzymatic Desymmetrization and Curtius Rearrangement of [alpha].[alpha]-Disubstituted Malonate Diesters" J. Org. Chem., 2010, 75, 1612-1619.

International Search report for International Application No. PCT/EP2009/003650, completed Jul. 20, 2009, dated Jul. 28, 2009, pp. 1-4.

Knorr, R. et al., "New Coupling Reagents in Peptide Chemistry", Tetrahedron Letters 30(15):1927-1930 (1989).

Nantermet, P.G. et al., "Design and Synthesis of Potent and Selective Macrocyclic Thrombin Inhibitors", Bioorganic & Medicinal Chemistry Letters 13:2781-2784 (2003).

Nicolaou, K.C. et al., "Metathesis Reactions in Total Synthesis", Angewandte Chemie Int. Ed. 44(29):4490-4527 (2005).

Nicolaou, I. et al., "Synthesis of N-Protected 1 H-Indole-5-Carboxylic Acids With Aldose Reductase Inhibitory Potential", Organic Preparations and Procedures International: The New Journal for Organic Synthesis 34(5):511-514 (2002).

Reddy, D.S. et al., "Synthesis and Conformational Studies of Dipeptides Constrained by Disubstituted 3-(Aminoethoxy)Propionic Acid Linkers", J. Org. Chem. 69:1716-1719 (2004).

Sartori, G. et al., "Product Class 8: Acyclic and Cyclic Ureas", Science of Synthesis 18:665-758 (2005).

Schwab, P. et al., "A Series of Well-Defined Metathesis Catalysts-Synthesis of [RuC12(=CHR')(PR3)2] and Its Reactions", Angew. Chem. Int. Ed. Engl. 34(18):2039-2041 (1995).

Sheehan, J.C., "A New Method of Forming Peptide Bonds", Communications to the Editor 77:1067-1068 (Feb. 20, 1955).

Simmons, H.E. et al., "A New Synthesis of Cyclopropanes from Olefins", Communications to the Editor 80:5323-5324 (Oct. 5, 1958).

Trnka, T. M. "The Development of L2X2Ru=CHR Olefin Metathesis Catalysts: An Organometallic Success Story" Accounts of Chemical Research, Jan. 2001, vol. 34, No. 1, pp. 18-29.

Tonge, Peter J. et al.; "Drug-Target Residence Time: Critical Information for Lead Optimization"; Curr Opin Chem Biol; Aug. 2010; 14(4): 467-474.

\* cited by examiner

MACROCYCLIC UREA DERIVATIVES AS INHIBITORS OF TAFIA, THEIR PREPARATION AND THEIR USE AS PHARMACEUTICALS

This application is a national stage application under 35 U.S.C. §371 of International Application No. PCT/EP2014/061669, filed Jun. 5, 2014, which claims the priority of European Application No. 13305779.4 filed on Jun. 10, 2013.

The present invention relates to macrocyclic urea derivatives of the formula I

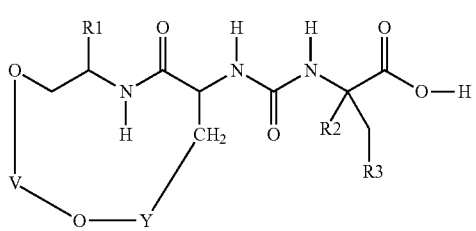

in which R1, R2, R3, V and Y are as defined below. The compounds of the formula I are inhibitors of the enzyme TAFIa (activated thrombin-activatable fibrinolysis inhibitor). The invention further relates to the process for the preparation of the compounds of formula I and to the use thereof as medicaments.

The enzyme TAFIa is produced for example through thrombin activation from the thrombin-activatable fibrinolysis inhibitor zymogen (TAFI). The enzyme TAFI is also referred to as plasma procarboxypeptidase B, procarboxypeptidase U or procarboxypeptidase R and is a proenzyme similar to carboxypeptidase B (L. Bajzar, Arterioscler. Thromb. Vasc. Biol. 2000, pages 2511-2518).

During formation of a clot, thrombin is generated as the final product of the coagulation cascade and induces conversion of soluble plasma fibrinogen to an insoluble fibrin matrix. At the same time, thrombin activates the endogenous fibrinolysis inhibitor TAFI. Activated TAFI (TAFIa) is thus produced during thrombus formation and lysis from the zymogen TAFI through the action of thrombin; thrombomodulin in a complex with thrombin increases this effect about 1250-fold. TAFIa cleaves basic amino acids at the carboxy end of fibrin. The loss of carboxy-terminal lysines as binding sites for plasminogen then leads to inhibition of fibrinolysis. Efficient inhibitors of TAFIa prevent the loss of these high-affinity lysine binding sites for plasminogen and, in this way, assist endogenous fibrinolysis by plasmin: TAFIa inhibitors have profibrinolytic effects.

In order to maintain hemostasis in the blood, mechanisms which lead to the clotting of blood and to the breaking up of clots have developed; these are in equilibrium. If a disturbed equilibrium favors coagulation, fibrin is produced in larger quantities, so that pathological processes of thrombus formation may lead to serious pathological states in humans.

Just like excessive coagulation may lead to serious pathological states caused by thrombosis, an antithrombotic treatment entails the risk of unwanted bleeding through disturbance of the formation of a necessary hemostatic plug. Inhibition of TAFIa increases endogenous fibrinolysis—without influencing coagulation and platelet aggregation—i.e. the disturbed equilibrium is shifted in favor of fibrinolysis. It is thus possible both to counter the buildup of a clinically relevant thrombus, and to increase the lysis of a pre-existing clot. On the other hand, buildup of a hemostatic plug is not impaired, so that a hemorrhagic diathesis is probably not to be expected (Bouma et al., J. Thrombosis and Haemostasis, 1, 2003, pages 1566-1574).

The TAFIa inhibitors of the invention are suitable for a prophylactic and for a therapeutic use in humans suffering from disorders associated with thromboses, embolisms, hypercoagulability or fibrotic changes. They can be employed for secondary prevention and are suitable both for acute and for long-term therapy.

Examples of TAFIa inhibitors have previously been described for example in the international applications WO2005105781, WO2007045339, WO2008067909, WO200066152, WO2003027128, WO200066557, WO2003106420, WO2003080631, WO200214285, WO2003061653, WO2003061652 and WO2003013526. WO2009146802 describes macrocyclic urea derivatives of the following general formula

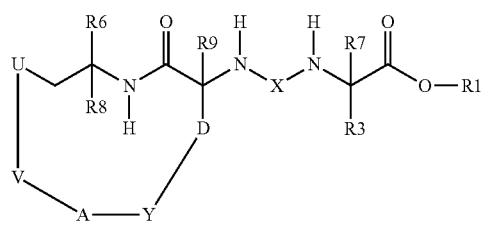

as inhibitors of TAFIa. However, WO2009146802 does not disclose the specific structure of the compounds of formula I according to our invention, especially not the essential alkyl-substitution as residue R2 in the formula I which corresponds to residue R7 in WO2009146802. The specific structure of the inventive compounds leads to an unexpected increase of the TAFIa inhibitor activity of our inventive compounds compared to the compounds described in WO2009146802 as shown below.

The invention therefore relates to the compounds of the formula I, in any of its stereoisomeric forms or a mixture of stereoisomeric forms in any ratio, or a pharmaceutically acceptable salt thereof,

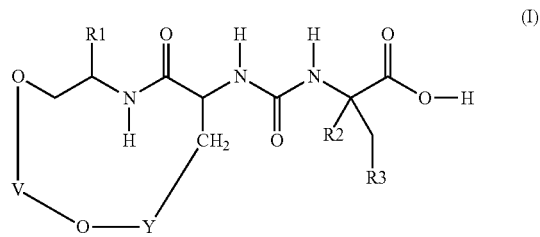

wherein
V is —$(C_2$-$C_9)$-alkylene-;
Y is a covalent bond or —$(C_6$-$C_{14})$-aryl-,
  wherein —$(C_6$-$C_{14})$-aryl- is unsubstituted or substituted independently of one another once, twice or three times by R15;
R1 is —$(C_1$-$C_6)$-alkyl, —$(C_0$-$C_4)$-alkylene-aryl or —$(C_0$-$C_4)$-alkylene-$(C_3$-$C_8)$-cycloalkyl,
  wherein alkyl, —$(C_0$-$C_4)$-alkylene, aryl and —$(C_3$-$C_8)$-cycloalkyl are unsubstituted or substituted independently of one another once, twice or three times by R16;

R2 is —($C_1$-$C_3$)-alkyl;
R3 is Het, substituted by —$NH_2$, or —($C_3$-$C_8$)-cycloalky, substituted by —$NH_2$,
  wherein Het is a 5-membered or 6-membered, monocyclic, aromatic heterocycle comprising 1 or 2 identical or different ring heteroatoms selected from the series consisting of nitrogen, oxygen and sulfur and wherein Het and —($C_4$-$C_8$)-cycloalkyl can additionally be substituted independently of one another once, twice or three times by R15;
R15 is hydrogen, —($C_1$-$C_4$)-alkyl, —O—$CF_3$, —$NH_2$, —OH, —$CF_3$ or halogen;
and
R16 is —O—$CF_3$, —$NH_2$, —OH, —$CF_3$ or halogen.

The present invention comprises all stereoisomeric forms of the compounds of the formula I, for example all enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I can all independently of one another have S configuration or R configuration. The invention relates to enantiomers, both the levorotatory and the dextrorotatory antipode, in enantiomerically pure form and essentially enantiomerically pure form, for example with a molar ratio of the two enantiomers of 98:2, or 99:1, or greater, and in the form of their racemate, i.e. a mixture of the two enantiomers in molar ratio of 1:1, and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form, for example with a molar ratio of the cis/trans isomers of 98:2, or 99:1, or greater, and in the form of mixtures of the cis isomer and the trans isomer in all ratios. Cis/trans isomerism can occur in substituted rings, for example. The preparation of individual stereoisomers, if desired, can be carried out by resolution of a mixture according to customary methods, for example, by chromatography or crystallization, or by use of stereochemically uniform starting compounds in the synthesis, or by stereoselective reactions. The separation of a mixture of stereoisomers can be carried out at the stage of the compound of the formula I or at the stage of an intermediate in the course of the synthesis. The invention also comprises all tautomeric forms of the compounds of the formula I.

If the compounds of the formula I comprise one or more acidic or basic groups, for example basic heterocyclic groups, the corresponding physiologically or toxicologically acceptable salts are also included in the invention, especially the pharmaceutically acceptable salts. The compounds of the formula I may thus be deprotonated on an acidic group. Compounds of the formula I comprising at least one basic group may also be prepared and used in the form of their acid addition salts, for example in the form of pharmaceutically acceptable salts with inorganic acids and organic acids. Salts can in general be prepared from acidic and basic compounds of the formula I by reaction with an acid or base in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange.

When a variable, for example R15, occurs more than once as a component, the definitions of the variables are independent from one another at each instance.

Alkyl radicals may be straight-chain or branched. This is also true when they bear substituents or occur as substituents of other radicals. Depending on the respective definition, the number of carbon atoms of an alkyl group can be 1, 2, 3, 4, 5 or 6, or 1, 2, 3 or 4, or 1, 2 or 3, or 1 or 2, or 1, for example. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl and hexyl.

A substituted alkyl group can be substituted in any positions by one or more identical or different substituents as specified in the definition of the respective group, provided that the resulting group or compound as a whole is sufficiently stable and is suitable as a pharmaceutically active compound. The prerequisite that a specific group and a compound of the formula I are sufficiently stable and suitable as a pharmaceutically active compound, applies in general with respect to the definitions of all groups in the compounds of the formula I. In one embodiment of the invention, a substituted alkyl group in any occurrence of the compounds of the formula I is, independent of any other occurrence, substituted by 1, 2 or 3 substituents, in another embodiment by 1 or 2 substituents, in another embodiment by 1 substituent.

The explanations with respect to alkyl groups apply correspondingly to alkyl groups which in the definition of a group in the compounds of the formula I are bonded to two adjacent groups, or linked to two groups, and may be regarded as divalent alkyl groups or alkylene groups. Besides in the case of the alkyl part of a substituted alkyl group, which may also be regarded as a divalent alkyl group, divalent alkyl groups occur in the groups —($C_2$-$C_9$)-alkylene- and —($C_0$-$C_4$)-alkylene-, for example, in which groups the terminal hyphens denote the free bonds via which the group is bonded. Thus, such divalent alkyl groups can also be straight-chain or branched, the bonds to the adjacent groups can be located in any positions and can start from the same carbon atom or from different carbon atoms. Examples of such divalent alkyl groups are methylene (—$CH_2$—), ethane-1,1-diyl (1,1-ethylene, —$CH(CH_3)$—), ethane-1,2-diyl (1,2-ethylene, —$CH_2$—$CH_2$—), propane-1,1-diyl (1,1-propylene, —$CH(CH_2$—$CH_3)$—), propane-1,2-diyl (1,2-propylene, —$CH(CH_3)$—$CH_2$—, —$CH_2$—$CH(CH_3)$—), propane-2,2-diyl (2,2-propylene, —$C(CH_3)_2$—), propane-1,3-diyl (1,3-propylene, —$CH_2$—$CH_2$—$CH_2$—), butane-1,1-diyl (1,1-butylene, —$CH(CH_2$—$CH_2$—$CH_3)$—), or butane-1,4-diyl (1,4-butylene, —$(CH_2)_4$—).

The number of ring carbon atoms in a —($C_3$-$C_8$)-cycloalkyl group can be 3, 4, 5, 6, 7 or 8. Examples of cycloalkyl are cyclopropyl, cyclobutyl, cyclopentyl, cyclohexyl, cycloheptyl and cyclooctyl, in one embodiment cyclobutyl and cyclopentyl. A substituted cycloalkyl group can be substituted in any positions by one or more identical or different substituents as specified in the definition of the respective group, provided that the resulting group or compound as a whole is sufficiently stable and is suitable as a pharmaceutically active compound.

A —($C_6$-$C_{14}$)-aryl group is a mono-, bi- or tricyclic aromatic group containing between 6 and 14 carbon atoms.

A —($C_6$-$C_{14}$)-aryl group can be unsubstituted or substituted as specified. A substituted —($C_6$-$C_{14}$)-aryl group can be substituted in any positions by one or more identical or different substituents as specified in the definition of the respective group, provided that the resulting group or compound as a whole is sufficiently stable and is suitable as a pharmaceutically active compound. Examples of aryl groups include phenyl, naphthyl, anthryl and phenanthryl, including the specific group of phenyl which is unsubstituted or substituted as specified.

A Het group or heteroaryl group is a 5-membered or 6-membered, monocyclic, aromatic heterocycle comprising 1 or 2 identical or different ring heteroatoms selected from the series consisting of nitrogen, oxygen and sulfur. A Het group can be unsubstituted or substituted as specified. A substituted Het group can be substituted in any positions by one or more identical or different substituents as specified in the definition of the respective group, provided that the resulting group or compound as a whole is sufficiently stable and is suitable as a pharmaceutically active compound. Examples of Het groups include pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophenyl, including the specific group of pyridin-2-yl, pyridin-3-yl, pyridin-4-yl, pyrimidin-2-yl, pyrimidin-4-yl, pyrimidin-5-yl, pyrazin-2-yl, pyridazin-3-yl, pyridazin-4-yl, pyrazol-3-yl, pyrazol-4-yl, imidazol-2-yl, imidazol-4-yl, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, pyrrol-2-yl, pyrrol-3-yl, furan-2-yl, furan-3-yl, thiophen-2-yl and thiophen-3-yl, which are all bonded via a ring carbon atom and which are all unsubstituted or substituted as specified.

Halogen is fluorine (F), chlorine (Cl), bromine (Br) or iodine (I).

Among the compounds of formula I that are subject of the present invention, mention may be made of the compounds of formula I, in any of its stereoisomeric forms or a mixture of stereoisomeric forms in any ratio, or a pharmaceutically acceptable salt thereof, wherein
V is —($CH_2$)$_4$—;
Y is a covalent bond or phenyl,
  wherein phenyl is unsubstituted or substituted independently of one another once, twice or three times by R15;
R1 is isopropyl;
R2 is methyl;
R3 is Het, substituted by —$NH_2$, or —($C_4$-$C_8$)-cycloalkyl, substituted by —$NH_2$,
  wherein Het is selected from pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophenyl, which are all bonded via a ring carbon atom and wherein Het and —($C_4$-$C_8$)-cycloalkyl can additionally be substituted independently of one another once, twice or three times by R15;
and
R15 is hydrogen, —($C_1$-$C_4$)-alkyl, —O—$CF_3$, —$NH_2$, —OH, —$CF_3$ or halogen.

Among the compounds of formula I that are subject of the present invention, mention may be made of the compounds of formula I, in any of its stereoisomeric forms or a mixture of stereoisomeric forms in any ratio, or a pharmaceutically acceptable salt thereof, wherein
V is —($CH_2$)$_4$—;
Y is a covalent bond or phenyl;
R1 is isopropyl;
R2 is methyl;
and
R3 is pyridinyl, substituted by —$NH_2$, cyclobutanyl, substituted by —$NH_2$, or cyclopentanyl, substituted by —$NH_2$.

Among the compounds of formula I that are subject of the present invention, mention may be made of the compounds of formula Ia or a pharmaceutically acceptable salt thereof

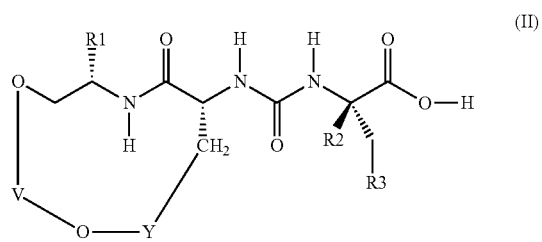

(II)

wherein V, Y, R1, R2 and R3 have the same meaning as described above.

In one embodiment V is defined as propandiyl, butandiyl or pentandiyl, for example —($CH_2$)$_4$—.

In another embodiment Y is defined as a covalent bond or phenyl, wherein phenyl is unsubstituted or substituted independently of one another once, twice or three times by R15. In another embodiment Y is defined as a covalent bond or phenyl.

In another embodiment R1 is defined as —($C_1$-$C_6$)-alkyl. In another embodiment R1 is defined as isopropyl.

In another embodiment R2 is defined as methyl.

In another embodiment R3 is defined as Het, substituted by —$NH_2$, or —($C_4$-$C_8$)-cycloalkyl, substituted by —$NH_2$, wherein Het is selected from pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophenyl, which are all bonded via a ring carbon atom, and wherein Het and —($C_4$-$C_8$)-cycloalkyl can additionally be substituted independently of one another once, twice or three times by R15. In another embodiment R3 is defined as is pyridinyl, substituted by —$NH_2$, cyclobutanyl, substituted by —$NH_2$, or cyclopentanyl, substituted by —$NH_2$.

In another embodiment R15 is defined as methyl, ethyl, —$CF_3$ or halogen, for example methyl.

Among the compounds of formula (I) that are subject matter of the invention, mention may be made in particular of the following compounds:
(S)-3-(6-Amino-pyridin-3-yl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid,
(S)-3-(3-Amino-cyclobutyl)-2-[3-((9S,12R)-9-isopropyl-11-oxo-2,7-dioxa-10-aza bicyclo[12.2.2]octadeca-1(17),14(18),15-trien-12-yl)-ureido]-2-methyl-propionic acid,
(S)-3-((1R,3R)-3-Amino-cyclopentyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid,
and
(S)-3-(6-Amino-pyridin-3-yl)-2-[3-((3S,6R)-3-isopropyl-5-oxo-1,8-dioxa-4-aza-cyclododec-6-yl)-ureido]-2-methyl-propionic acid.

Another subject of the present invention are processes for the preparation of the compounds of the formula I which are outlined below and by which the compounds of the formula I and intermediates occurring in the course of their synthesis are obtainable. In accordance with the invention the compounds of general formula (I) can be prepared by the following processes:

Process a:

Reacting a compound of formula VII

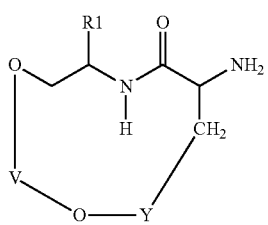

VII with a compound of the formula VIII

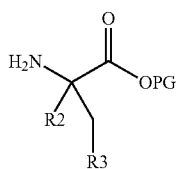

VIII and with phosgene or a phosgene equivalent like carbonyl diimidazole (CDI) or similar reagents in aprotic solvents such as DMF, THF, CH$_2$Cl$_2$ or other similar solvents, eventually in presence of a base such as K$_2$CO$_3$, Na$_2$CO$_3$, triethylamine, diisopropylamine (DIPEA), pyridine or others, at temperatures between 0° C. and 140° C. to give a compound of the formula XII

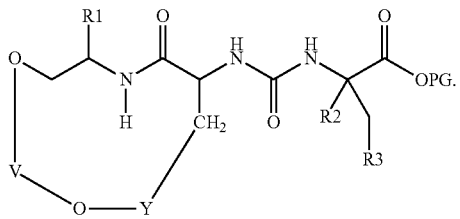

XII

PG is a suitable ester protective group radical, and the nitrogen in R3 is protected where appropriate by a suitable amino protective group.

The protecting group PG forms together with the acid of the compound of formula XII a suitable ester and is for example an alkyl group, such as methyl or ethyl, or benzyl.

The nitrogen in R3 can be protected where appropriate by a variety of amino protecting groups e.g. those mentioned in T. W. Greene and P. G. M. Wuts: Protective Groups in Organic Synthesis, Third Edition, John Wiley and Sons, New York, 1999, 518-525, 531-540. The amino protecting group chosen is stable under the basic reaction conditions and can be selected e.g. from carbamates, such as tert-butyloxycarbonyl and benzyloxycarbonyl or p-methoxybenzylcarbonyl, amides, such as N-formyl or N-acetyl, N-alkylaryls such as N-benzyl, N-1-(diphenyl)methyl, N-trityl or (4-methoxyphenyl)diphenylmethyl or N—P and N-sulfonyl protecting groups such as N-dialkyl phosphoramidates and N-p-toluenesulfonyl. In one embodiment the protecting group is tert-butyloxycarbonyl.

Other carboxyl- and amino protecting groups which can be used are for example described in T. W. Greene and P. G. M. Wuts: Protective Groups in Organic Synthesis, Third Edition, John Wiley and Sons, New York, 1999.

Subsequently the protective group PG and the protective group which is present where appropriate on the nitrogen in R3 are eliminated, resulting in the compound of the formula I.

The protective groups can be eliminated for example under acidic or basic conditions or by hydrogenolysis in polar protic solvents such as water, alcohols and ethers or in suitable aprotic solvents like CH$_2$Cl$_2$, C$_2$H$_4$Cl$_2$ or in mixtures of the mentioned solvents. Suitable acids are exemplified by HCl, trifluoracetic acid, acetic acid. Suitable bases are exemplified by metal hydroxides such as NaOH, metal carbonates such as K$_2$CO$_3$, or organic bases like piperidine or triethylamine. Hydrogenolysis can be conducted under H$_2$ atmosphere at 0-4 bar under application of a transition metal catalyst, for example palladium on charcoal. Reactions can be performed at temperatures typically between 40° C. and 120° C.

The compound of formula VIII can be prepared by reacting a compound of the formula XI

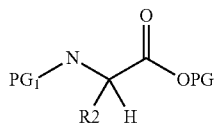

XI with LG-CH$_2$—R3 in presence of a base in polar aprotic solvents like DMF, THF or DMSO, at temperatures between −78° C. and 100° C. to give a compound of formula VIII.

The residue LG in alkylating agent of formula LG-CH$_2$—R3 is a suitable leaving group and can be selected from halogens such as chloro, bromo, iodo or from sulfonyl esters such as mesylate, tosylate, nosylate, brosylate, triflate or nonaflate. In one embodiment the residue LG is selected from bromo and chloro.

The nitrogen in R3 is protected where appropriate by a suitable amino protective group as mentioned above The protecting group PG can form together with the acid of the compound of formula XI a suitable ester and is defined as described above for the compound of formula XII.

The amino protective group PG$_1$ is exemplified by but not limited to benzhydrylene and other imine type protecting groups. Other examples are described in T. W. Greene and P. G. M. Wuts: Protective Groups in Organic Synthesis, Third Edition, John Wiley and Sons, New York, 1999.

Suitable bases are all bases that are strong enough to form the enolate anion from the compound of formula XI. Examples for such bases are alkali metal amides, metal hydrides, or alkoxides. In one embodiment the bases can be alkali metal hexamethyldisilazide (MHMDS) or lithium base (LiHMDS), which can be obtained commercially. Other bases which can be used are lithium diisopropylamide (LDA) or alkali alkoxides, such as lithium-, sodium- or potassium-tert-butoxide or lithium-, sodium- or potassium ethoxide. In another embodiment, sodium hydride (NaH) can be used.

R1, R2, R3, V and Y in the compounds of formulae VII, VIII, XI and XII and in the compound LG-CH$_2$—R3 are defined as described above for the compound of formula I. As mentioned above the nitrogen in R3 can be protected where appropriate by a suitable amino protective group as defined above.

Process b:

Reacting a compound of the formula XIII

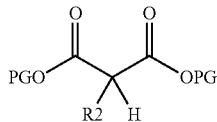

XIII with LG-CH$_2$—R3 in presence of a base to give a compound of formula XIV

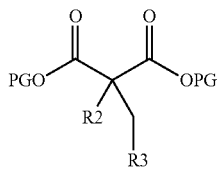

XIV

The protecting groups PG on both acid groups are independently from each other selected from suitable ester protective groups like alkyl, allyl or benzyl, for example methyl, ethyl, propyl, butyl or tert-butyl. In one embodiment the protecting groups in the compounds of formulae XIII and XIV are selected in such a way that one PG is ethyl and the other PG is tert-butyl.

The residue LG in alkylating agent of formula LG-CH$_2$—R3 can be selected from halogens such as chloro, bromo, iodo or from sulfonyl esters such as mesylate, tosylate, nosylate, brosylate, triflate or nonaflate. In one embodiment the residue LG is selected from bromo and chloro.

The nitrogen in R3 can be protected where appropriate by a variety of amino protecting groups as described above in process a.

Suitable bases are all bases that are strong enough to form the enolate anion from the compound of formula VIII. Examples for such bases are alkali metal amides, metal hydrides, or alkoxides. In one embodiment the bases can be alkali metal hexamethyldisilazide (MHMDS) or lithium base (LiHMDS), which can be obtained commercially. Other bases are lithium diisopropylamide (LDA) or alkali alkoxides, such as lithium-, sodium- or potassium-tert-butoxide or lithium-, sodium- or potassium ethoxide.

Solvents which can be used are solvents compatible with the basic reaction conditions, such as ethers or alcohols. Ethers are exemplified by, but not limited to tetrahydrofuran (THF), methyl-tert.-butyl ether (MTBE), dioxane, dimethoxymethane (DME) or 2-methyl tetrahydrofuran. In one embodiment THF is used. Alcohols are exemplified by, but not limited to methyl alcohol (MeOH), ethyl alcohol (Ethanol), propyl alcohol (PrOH), iso-propyl alcohol (iPrOH), butyl alcohol (BuOH) and tert-butyl alcohol (tBuOH). In one embodiment ethanol is used.

The reaction temperature is ranging from −78° C. to 100° C. depending on the freezing point and the boiling point of the solvent as well as on the nature of base used in the reaction step.

Followed by selectively removing of one of the protective groups in the compound of formula XIV by the treatment with a hydroxide base MOH to give a compound of the formula XV

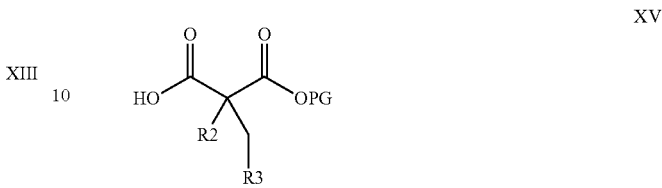

XV where M is Li, Na, or K, in one embodiment sodium, in a protic solvent like water or alcohols, in one embodiment ethanol if PG is ethyl.

Reacting a compound of formula XV afterwards with an azide source, exemplified by, but not limited to diphenylphosphoryl azide (DPPA), in the presence of a base in a suitable solvent to give a compound of the formula XVI

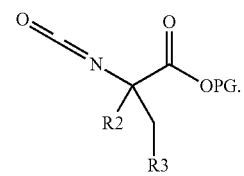

XVI

Bases which can be used are tertiary amines, for example triethyl amine, diisopropylethylamine or tributylamine. Solvents which can be used are aprotic solvents like ethers, esters, acetonitrile or benzene derivatives. The temperature used is ranging from −20° C. to 100° C. depending on the freezing point and the boiling point of the solvent.

Subsequently reacting the compound of the formula XVI with a compound of formula VII to give a compound of the formula XII.

Solvents which can be used are the same as described for the preparation of the compounds of formula XVI. The temperature used is ranging from 20-140° C. depending on the freezing point and the boiling point of the solvent.

Subsequently the protective group PG and the protective group which is present where appropriate on the nitrogen in R3 are eliminated, resulting in the compound of the formula I. The protective groups can be eliminated as described in process a.

The compounds of formula VII in processes a and b can also be used in form of their salts, exemplified by, but not limited to the hydrochloride or trifluoroacetate salts. If salts of formula VII are used an additional equivalent of the base is needed, for example tertiary amines such as triethyl amine, diisopropylethylamine or tributylamine.

R1, R2, R3, V and Y in the compounds of formulae VII, XII, XIII, XIV, XV and XVI and in the compound LG-CH$_2$—R3 used in processes a and b are defined as described above for the compound of formula I. As mentioned above the nitrogen in R3 can be protected where appropriate by a suitable amino protective group as defined above.

The compound of the formula I can either be isolated in free form prepared by processes a) or b) or converted into physiologically tolerated salts in the case where acidic or basic groups are present.

As is usual and applies to all reactions performed in the course of the synthesis of a compound of the formula I, appropriate details of the conditions applied in a specific preparation process, including the solvent, a base or acid, the temperature, the order of addition, the molar ratios and other parameters, are routinely chosen by the skilled person in view of the characteristics of the starting compounds and the target compound and the other particularities of the specific case. As is also known to the skilled person, not all processes described herein will in the same way be suitable for the preparation of all compounds of the formula I and their intermediates, and adaptations have to be made. In all processes for the preparation of the compounds of the formula I, workup of the reaction mixture and the purification of the product is performed according to customary methods known to the skilled person which include, for example, quenching of a reaction mixture with water, adjustment to a certain pH, precipitation, extraction, drying, concentration, crystallization, distillation and chromatography including high performance liquid chromatography (HPLC). Also for the characterization of the products, customary methods are used such as NMR, IR and mass spectroscopy.

The starting materials employed in the processes outlined above, e.g. the compounds of formula XI and LG-CH$_2$—R3, are commercially available or can be prepared according to procedures, or in analogy to procedures, described in the literature. For example, Compounds of formula VII can be prepared as described in WO2009146802 or via similar processes. The compounds of formula XIII can for example be prepared as described in U. Aeberhard et al. Helv. Chim. Acta 1983, 66, 2740.

EXPERIMENTAL PART

List of Abbreviations

DIPEA N,N-diisopropylethylamine
DMF Dimethylformamide
LiHMDS Lithium bis(trimethylsilyl)amide
min Minute(s)
R$_t$ Retention time
RT Room temperature
TFA Trifluoroacetic acid
THF Tetrahydrofuran Final products were normally determined by mass spectroscopic methods (FAB-, ESI-MS) and $^1$H-NMR; the main peak or two main peaks were indicated in each case. Temperatures are stated in degrees Celsius, RT means room temperature (21° C. to 24° C.). Abbreviations used are either explained or correspond to usual conventions.

Unless stated otherwise, the LC-MS analyses were carried under the following conditions:
Method A: column: YMC Jsphere ODS H80 20×2.1 mm, packing material 4 μm, mobile phase: CH$_3$CN+0.05% trifluoroacetic acid (TFA): H$_2$O+0.05% TFA, gradient: 4:96 (0 min) to 95:5 (2.0 min), flow rate: 1 ml/min, temperature: 30° C.
Method B: column: Luna C18 10×2 mm, packing material 3 μm, mobile phase: CH$_3$CN+0.05% trifluoroacetic acid (TFA): H$_2$O+0.05% TFA, gradient: 7:93 (0 min) to 95:5 (1.2 min), flow rate: 1.1 ml/min, temperature: 30° C.
Method C: column: Waters UPLC BEH C18 50×2.1 mm, packing material 1.7 μm, mobile phase: CH$_3$CN+0.08% formic acid (FA): H$_2$O+0.1% FA, gradient: 5:95 (0 min) to 95:5 (1.1 min), flow rate: 0.9 ml/min, temperature: 55° C.

Unless indicated otherwise, chromatographic separations were carried out on silica gel with ethyl acetate/heptane mixtures as mobile phase, and preparative separations on reversed phase (RP) silica gel (HPLC) with trifluoroacetic acid-containing water/acetonitrile mixtures as mobile phase.

Solvents were evaporated off usually under reduced pressure at 35° C. to 45° C.

Example 1

(S)-3-(6-Amino-pyridin-3-yl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid

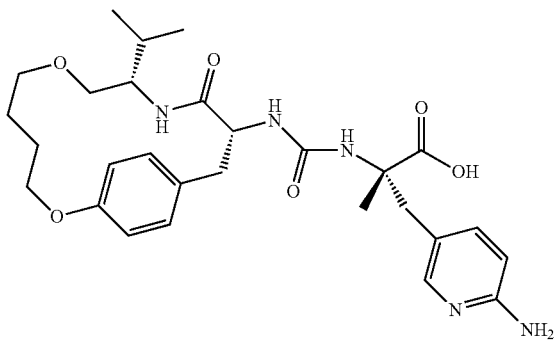 [SMILES: CC(C)[C@H]1COCCCCOc2ccc(cc2)C[C@@H](NC(=O)N[C@@](C)(Cc2ccc(N)nc2)C(=O)O)C(=O)N1]

A. (R)-2-(6-tert-Butoxycarbonylamino-pyridin-3-ylmethyl)-2-methyl-malonic acid tert-butyl ester ethyl ester (A compound of formula XIV)

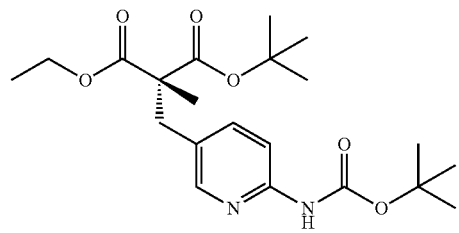 [SMILES: CCOC(=O)[C@@](C)(Cc1ccc(NC(=O)OC(C)(C)C)nc1)C(=O)OC(C)(C)C]

60.0 g (297 mmol) 2-Methyl-malonic acid tert-butyl ester ethyl ester (compound of formula XIII) were dissolved in 800 ml THF. To this solution were added 297 ml (297 mmol) LiHMDS (1 M solution in methyl tert-butyl ether) with water bath cooling. After 30 minutes 66.6 g (275 mmol) (5-Chloromethyl-pyridin-2-yl)-carbamic acid tert-butyl ester were added in portions and the mixture was stirred for 90 minutes at RT. The mixture was added to 800 ml water and aqueous NH$_4$Cl-solution. The solvents were removed and the resulting solid was filtered and air-dried to yield the crude product in quantitative yield.

LC/MS (method A): R$_t$=1.74 min, m/z: 409.20 [Mh$^+$].

The crude product was submitted to chiral preparative HPLC (AD-H-30, 250×30 mm, EtOH/MeOH 1:1, 24 ml/min) to yield 40 g (33% yield) of the chiral diester.

Chiral HPLC: (Chiralpak AD-H/39 (250×4.6 mm), EtOH/MeOH 1:1, 30° C., 1 ml/min): R$_t$=4.31 min.

B. (R)-2-(6-tert-Butoxycarbonylamino-pyridin-3-ylmethyl)-2-methyl-malonic acid mono tert-butyl (A compound of formula XV)

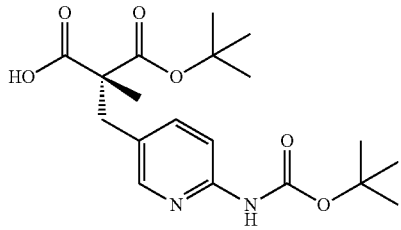 [SMILES: CC(C)(C)OC(=O)Nc1ccc(C[C@](C)(C(=O)O)C(=O)OC(C)(C)C)cn1]

40 g (98 mmol) (R)-2-(6-tert-Butoxycarbonylamino-pyridin-3-ylmethyl)-2-methyl-malonic acid tert-butyl ester ethyl ester (compound from step A) were dissolved in 560 ml THF and 200 ml MeOH. To this solution were added 25 g (0.59 mol) LiOH×H₂O in 210 ml water and the mixture was stirred for 14 hours at 30° C. The pH was adjusted to 3 by addition of aqueous NaHSO₄, the organic solvents were removed and the solid was filtered and air-dried to yield the acid in quantitative yield.

LC/MS (method A): $R_t$=1.39 min, m/z: 381.20 [MH⁺], 325.10 [MH⁺-tBu].

C. (S)-3-(6-tert-Butoxycarbonylamino-pyridin-3-yl)-2-isocyanato-2-methyl-propionic acid tert-butyl ester (A compound of formula XVI)

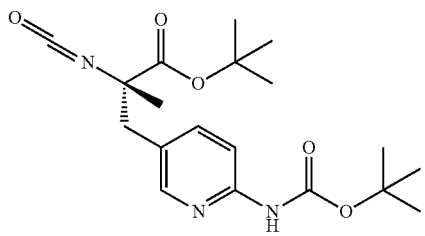 [SMILES: CC(C)(C)OC(=O)Nc1ccc(C[C@](C)(N=C=O)C(=O)OC(C)(C)C)cn1]

30.3 g (79.7 mmol) of the acid from step B and 17.1 ml (95.7 mmol) N,N-diisopropyl ethyl amine were dissolved in 300 ml MeCN and heated to 70° C. 17.3 ml (79.7 mmol) diphenylphosphoryl azide were slowly added and the mixture was stirred for 4 hours at 70° C. The obtained isocyanate-solution was directly used in the next step.

LC/MS (method A): $R_t$=1.76 min, m/z: 378.20 [MH⁺], 322.10 [MH⁺-tBu].

D. (S)-3-(6-tert-Butoxycarbonylamino-pyridin-3-yl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid tert-butyl ester (A compound of formula XII)

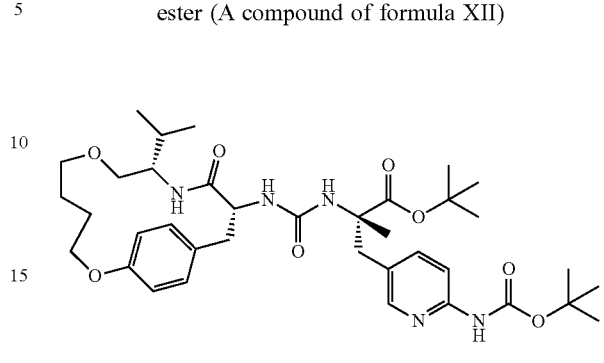

To the isocyanate-solution (from step C) were added 25.6 g (79.7 mmol) of (9S,12R)-12-Amino-9-isopropyl-2,7-dioxa-10-aza-bicyclo[12.2.2]octadeca-1(17),14(18),15-trien-11-one (A compound of formula VII) at 45° C. and the mixture was stirred for 18 hours at 45° C. After cooling to RT, 150 ml phosphate buffer (pH 7) were added and the solvent was removed. The product was extracted twice with ethylacetate. The combined organic layers were successively washed with aqueous NaHSO₄, aqueous NaHCO₃ and brine, dried with MgSO₄ and concentrated. 47.6 g (86% yield) of the urea were obtained after crystallisation from methyl tert-butyl ether.

LC/MS (method A): $R_t$=1.66 min, m/z: 698.40 [MH⁺].

E (S)-3-(6-Amino-pyridin-3-yl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid (A compound of formula II)

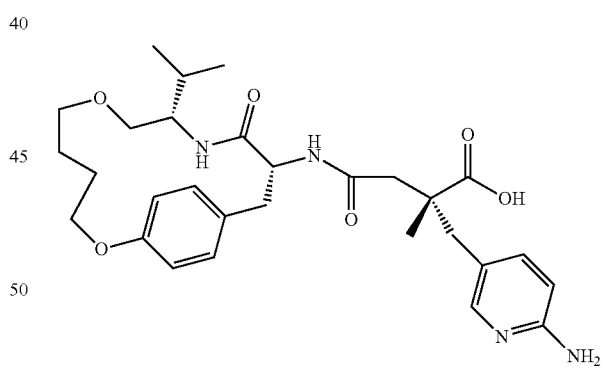

47.6 g (68.2 mmol) of (S)-3-(6-tert-Butoxycarbonylamino-pyridin-3-yl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid tert-butyl ester (Compound from step D) were dissolved in 250 ml THF and treated with 350 ml half concentrated aqueous HCl. The mixture was stirred for 6 hours at 45° C. After stirring the mixture was concentrated and the residue was distilled twice with 400 ml water. The crude product was dissolved in acetone/water and 68.2 ml (136 mmol) of aqueous sodium hydroxide were added. The solvent was removed and the residue was filtered over 540 g SPE-column (Supelco Dianion HP-20SS, water, water/acetone). The product was concentrated and crystallised from acetone/water to yield 18.5 g (48% yield) of the title compound as a sodium salt.

LC/MS (method A): R$_t$=1.14 min, m/z: 542.30 [MH$^+$].

$^1$H-NMR (DMSO-d6, 400 MHz) δ[ppm]=0.68 (d, 3H), 0.73 (d, 3H), 1.36 (s, 3H), 1.38-1.71 (m, 5H), 2.62-2.71 (m, 2H), 2.79 (dd, 1H), 2.86 (d, 1H), 3.01 (dd, 1H), 3.15 (d, 1H); 3.19-3.35 (m, 3H, signal overlaid by water), 4.14-4.29 (m, 3H), 5.52 (bs, 2H), 6.13 (d, 1H), 6.28 (d, 1H), 6.47 (d, 1H), 6.66 (s, 3H), 6.81-6.89 (m, 3H), 7.13-7.20 (m, 2H), 7.65 (d, 1H).

Example 2

(S)-3-trans-(3-Amino-cyclobutyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid

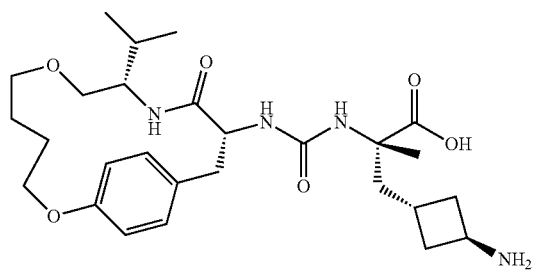 [SMILES: CC(C)[C@H]1COCCCCOc2ccc(cc2)C[C@@H](NC(=O)N[C@@](C)(C[C@H]2C[C@H](N)C2)C(=O)O)C(=O)N1]

A. (S)-2-(Benzhydrylidene-amino)-propionic acid tert-butyl ester

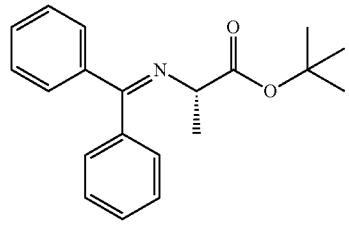 [SMILES: C[C@H](N=C(c1ccccc1)c1ccccc1)C(=O)OC(C)(C)C]

13.81 g (76 mmol) L-Alanine-tert-butyl ester hydrochloride were dissolved in 50 ml dichloromethane. 13.78 g (76 mmol) Benzophenon imine were added. The resulting mixture was stirred overnight at room temperature. The reaction mixture was diluted with water and dichloromethane. The organic phase was washed with brine, dried over anhydrous MgSO$_4$ and concentrated under vacuum to give crude (S)-2-(benzhydrylidene-amino)-propionic acid tert-butyl ester in quantitative yield.

LC/MS (method B): R$_t$=0.75 min, m/z: 310.3 [MH$^+$].

B. Tert-Butyl trans-3-iodomethyl-cyclobutyl-carbamate

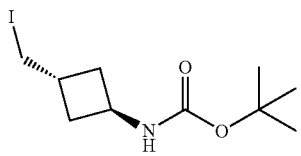

To a solution of 8.0 g (39.8 mmol) tert-Butyl trans-3-hydroxymethyl-cyclobutyl-carbamate in 150 ml dichloromethane were added at 0° C. 2.98 g (43.7 mmol) imidazole, 11.47 g (43.7 mmol) triphenylphosphine and 11.1 g (43.7 mmol) iodine. After stirring for 1 hour at 0° C. the reaction mixture was concentrated under vacuum. The resulting residue was purified by flash chromatography using a n-heptane/ethylacetate eluent to give 10.3 g pure tert-Butyl trans-3-iodomethyl-cyclobutyl-carbamate (84% yield).

The material was used in the next step without further characterization.

C. (S)-2-(Benzhydrylidene-amino)-3-trans-(3-tert-butoxycarbonylamino-cyclobutyl)-2-methyl-propionic acid tert-butyl ester (A compound of formula XI)

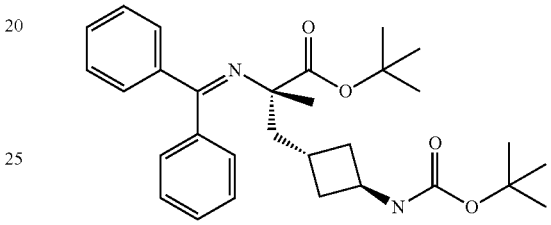

5.7 g (18.4 mmol) (S)-2-(Benzhydrylidene-amino)-propionic acid tert-butyl ester (compound of step A) were dissolved in 45 ml THF. At 0° C. under argon atmosphere 13.8 ml of a 2 M NaHMDS-solution (27.6 mmol) in THF were added dropwise. After 30 minutes a solution of 6.01 g (19.3 mmol) tert-butyl-trans-3-iodomethyl-cyclobutyl-carbamate (compound of step B) in 20 ml THF were added within 10 minutes. The reaction mixture was stirred for 3 hours at room temperature and then quenched with 50 ml of a saturated NH$_4$Cl solution. The resulting mixture was extracted twice with 200 ml ethyl acetate. The combined organic phases were washed with brine, dried over anhydrous Na$_2$SO$_4$ and concentrated under reduced pressure. Purification by flash chromatography using a n-heptane/ethyl acetate eluent gave 1.7 g pure 2-(benzhydrylideneamino)-3-trans-(3-tert-butoxycarbonylamino-cyclobutyl)-2-methyl-propionic acid tert-butyl ester as racemate. Further chromatography using a chiral stationary phase (Chiralpak IC 250×30 mm 5μ) and CO$_2$/Isopropanol as a mobile phase gave 450 mg of pure (S)-2-(benzhydrylidene-amino)-3-trans-(3-tert-butoxycarbonylamino-cyclobutyl)-2-methyl-propionic acid tert-butyl ester.

LC/MS (method B): R$_t$=0.93 min, m/z: 493.2 [MH$^+$].

D. (S)-2-Amino-3-trans-(3-tert-butoxycarbonylamino-cyclobutyl)-2-methyl-propionic acid tert-butyl ester (A compound of formula VIII)

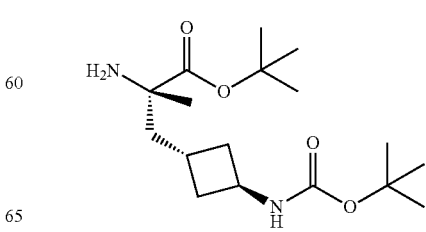

380 mg (0.77 mmol) (S)-2-(benzhydrylidene-amino)-3-trans-(3-tert-butoxycarbonylamino-cyclobutyl)-2-methyl-propionic acid tert-butyl ester (Compound of step C) were dissolved in 30 ml methanol. Under Argon 125 mg palladium on charcoal (10%) were added. The argon atmosphere was replaced by hydrogen and the resulting mixture was stirred for 4 hours at room temperature. The reaction mixture was filtered over celite and concentrated under reduced pressure to give 250 mg of crude (S)-2-amino-3-trans-(3-tert-butoxycarbonylamino-cyclobutyl)-2-methyl-propionic acid tert-butyl ester ester as yellow oil (99% yield).

LC/MS (method B): $R_t$=0.68 min, m/z: 329.2 [MH$^+$].

E (S)-3-trans-(3-tert-Butoxycarbonylamino-cyclobutyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid tert-butyl ester (A compound of formula XII)

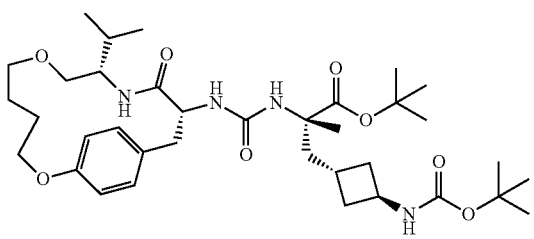 [SMILES: CC(C)[C@H]1COCCCCOc2ccc(cc2)C[C@@H](NC(=O)N[C@@](C)(C[C@H]2C[C@H](NC(=O)OC(C)(C)C)C2)C(=O)OC(C)(C)C)C(=O)N1]

250 mg (0.76 mmol) crude (S)-2-amino-3-trans-(3-tert-butoxycarbonylamino-cyclobutyl)-2-methyl-propionic acid tert-butyl ester ester (Compound of step D) were dissolved in 6 ml DMF. 129 μl (0.76 mmol) N,N-diisopropylethylamine (DIPEA) were added. At 0° C. 123 mg (0.76 mmol) 1,1'-carbonyldiimidazole (CU) were added and the resulting mixture was stirred for 30 min. Then a solution of 244 mg (0.76 mmol) (9S,12R)-12-Amino-9-isopropyl-2,7-dioxa-10-aza-bicyclo[12.2.2]octadeca-1(17),14(18),15-trien-11-one (A compound of formula VII) in 2 ml DMF were added dropwise. After stirring for 1 hour at 0° C. and 10 hours at room temperature the mixture was concentrated under reduced pressure and purified by preparative RP-HPLC (CH$_3$CN/H$_2$O gradient+0.1% TFA). 115 mg (S)-3-trans-(3-tert-butoxycarbonylamino-cyclobutyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid tert-butyl ester (22% yield) were obtained.

LC/MS (method B): $R_t$=1.07 min, m/z: 675.3 [MH$^+$].

F (S)-3-trans-(3-Amino-cyclobutyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid (A compound of formula II)

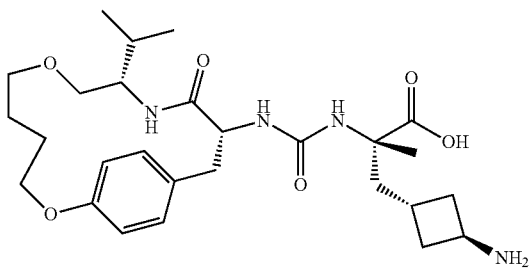 [SMILES: CC(C)[C@H]1COCCCCOc2ccc(cc2)C[C@@H](NC(=O)N[C@@](C)(C[C@H]2C[C@H](N)C2)C(=O)O)C(=O)N1]

115 mg (170 μmol) (S)-3-trans-(3-tert-butoxycarbonylamino-cyclobutyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid tert-butyl ester (Compound of step E) were dissolved in a mixture of 9.5 ml TFA, 0.25 ml H$_2$O and 0.25 ml triisopropyl-silane and stirred for 2 hours at room temperature. The mixture was concentrated under reduced pressure and purified by preparative RP-HPLC (CH$_3$CN/H$_2$O gradient+0.1% TFA) to give 86 mg pure (S)-3-trans-(3-amino-cyclobutyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid as trifluoroacetate in form of a colorless amorphous material (80% yield).

LC/MS (method B): $R_t$=0.62 min, m/z: 519.3 [MH$^+$].

$^1$H-NMR (DMSO-d6, 400 MHz) δ[ppm]=12.80 (1H, s, br), 7.90 (3H, s, br), 7.22 (1H, d), 6.91 (3H, m), 6.61 (1H, s), 6.39 (1H, d), 5.87 (1H, d), 4.29 (1H, m), 4.20 (2H, m), 3.69 (1H, m), 3.25 (4H, t), 3.08-3.15 (1H, dd), 2.80-2.91 (2H, dd), 2.60 (1H, dd), 2.18-2.28 (1H, m), 1.95-2.19 (4H, m), 1.92 (1H, m), 1.69 (1H, m), 1.49-1.62 (3H, m) 1.38 (3H, s), 0.73 (3H, d), 0.70 (3H, d).

Example 3

(S)-3-((1R,3R)-3-Amino-cyclopentyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid

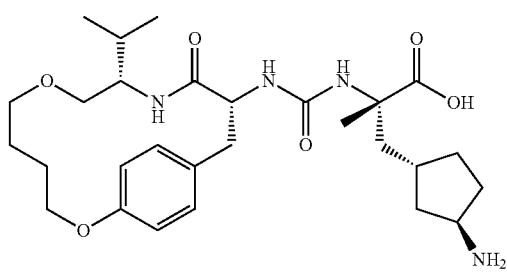 [SMILES: CC(C)[C@H]1COCCCCOc2ccc(cc2)C[C@@H](NC(=O)N[C@@](C)(C[C@@H]2CC[C@@H](N)C2)C(=O)O)C(=O)N1]

A. ((1S,3S)-3-Hydroxymethyl-cyclopentyl)-carbamic acid tert-butyl ester

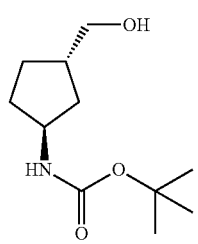

5.0 g (20.55 mmol) (1S,3S)-3-tert-Butoxycarbonylamino-cyclopentanecarboxylic acid methyl ester were dissolved in 15 ml THF. Under argon atmosphere 3.3 g (82.2 mmol) LiAlH$_4$ were added portionwise at 0° C. The resulting mixture was stirred for 2 hours and then carefully quenched with water. The mixture was extracted with ethyl acetate. The combined organic layers were washed with brine and concentrated under reduced pressure to give crude 4.25 g ((1S,3S)-3-Hydroxymethyl-cyclopentyl)-carbamic acid tert-butyl ester (97% yield).

The material was used in the next step without further characterization.

B. ((1S,3S)-3-Iodomethyl-cyclopentyl)-carbamic acid tert-butyl ester

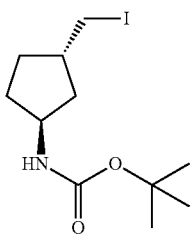

To a solution of 2.1 g (9.7 mmol) tert((1S,3S)-3-Hydroxymethyl-cyclopentyl)-carbamic acid tert-butyl ester (Compound from step A) in 40 ml dichloromethane were added at 0° C. 724 mg (10.6 mmol) imidazole, 2.8 g (10.6 mmol) triphenylphosphine and 2.7 g (10.6 mmol) iodine. After stirring for 1 hour at 0° C. the reaction mixture was concentrated under vacuum. The resulting residue was purified by flash chromatography using a n-heptane/ethylacetate eluent to give 2.4 g pure ((1S,3S)-3-Iodomethyl-cyclopentyl)-carbamic acid tert-butyl ester (75% yield).

The material was used in the next step without further characterization.

C. (RS)-2-(Benzhydrylidene-amino)-3-((1R,3R)-3-tert-butoxycarbonylaminocyclopentyl)-2-methyl-propionic acid tert-butyl ester (A compound of formula XI)

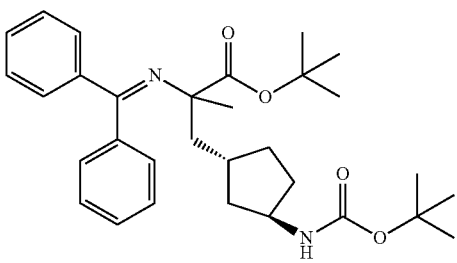 [SMILES: CC(C)(C)OC(=O)N[C@@H]1CC[C@@H](CC(C)(N=C(c2ccccc2)c2ccccc2)C(=O)OC(C)(C)C)C1]

1.0 g (3.2 mmol) (S)-2-(Benzhydrylidene-amino)-propionic acid tert-butyl ester (Compound from example 2, step A) were dissolved in 20 ml THF. At 0° C. under argon atmosphere 2.4 ml of 2 M NaHMDS-solution (4.8 mmol) in THF were added within 10 minutes. After 30 minutes 1.1 g (3.4 mmol) ((1S,3S)-3-Iodomethyl-cyclopentyl)-carbamic acid tert-butyl ester (Compound from step B) in 5 ml THF were added slowly. The reaction mixture was stirred for 4 hours at room temperature and then quenched with 10 ml of a saturated NH$_4$Cl solution. The resulting mixture was extracted twice with 50 ml ethyl acetate. The combined organic phases were washed with brine, dried over anhydrous Na$_2$SO$_4$ and concentrated under reduced pressure. Purification by flash chromatography using a n-heptane/ethyl acetate eluent gave 1.3 g 2-(benzhydrylidene-amino)-3-((1R,3R)-3-tert-butoxycarbonylaminocyclopentyl)-2-methyl-propionic acid tert-butyl ester as racemate (80% yield).

LC/MS (method B): R$_t$=0.93 min, m/z: 507.20 [MH$^+$].

D (RS)-2-Amino-3-((1R,3R)-3-tert-butoxycarbonylamino-cyclopentyl)-2-methyl-propionic acid tert-butyl ester (A compound of formula VIII)

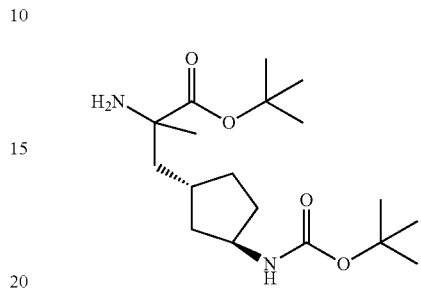

1.28 g (2.5 mmol) racemic 2-(benzhydrylidene-amino)-3-((1R,3R)-3-tert-butoxycarbonylaminocyclopentyl)-2-methyl-propionic acid tert-butyl ester (Compound of step C) were dissolved in 100 ml methanol. Under Argon 670 mg palladium on charcoal (10%) were added. The argon atmosphere was replaced by hydrogen and the resulting mixture was stirred for 24 hours at room temperature. After filtration of the catalyst 670 mg fresh palladium on charcoal were added and the reaction mixture was stirred for another 4 hours under a hydrogen atmosphere. The reaction mixture was filtered over celite and concentrated under reduced pressure. The resulting residue was purified by flash chromatography using a n-heptane/ethyl acetate eluent (addition of 1% triethyl amine) to give 312 mg of racemic 2-amino-3-((1R,3R)-3-tert-butoxycarbonylamino-cyclopentyl)-2-methyl-propionic acid tert-butyl ester (36% yield).

LC/MS (method B): R$_t$=0.68 min, m/z: 343.2 [MH$^+$].

E (RS)-3-((1R,3R)-3-tert-Butoxycarbonylamino-cyclopentyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid tert-butyl ester (A compound of formula XII)

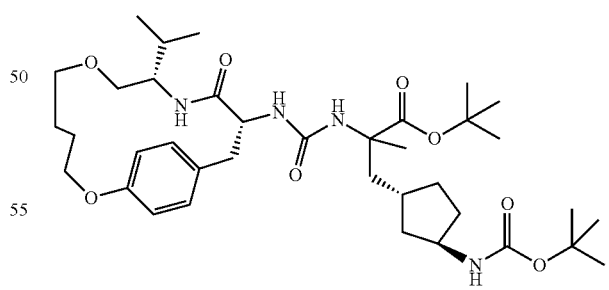

100 mg (0.31 mmol) (9S,12R)-12-Amino-9-isopropyl-2,7-dioxa-10-aza-bicyclo[12.2.2]octadeca-1(17),14(18),15-trien-11-one (A compound of formula VII) were dissolved in 3 ml DMF. 53 µl (0.31 mmol) DIPEA were added. At 0° C. 50.6 mg (0.31 mmol) 1,1'-carbonyldiimidazole (CU) were added and the resulting mixture was stirred for 30 minutes. Then a solution of 107 mg (0.31 mmol) racemic 2-amino-3-((1R,3R)-3-tert-butoxycarbonylamino-cyclopentyl)-2- methyl-propionic acid tert-butyl ester (Compound from step D) 53 µl (0.31 mmol) N,N-diisopropylethylamine (DIPEA) in 1 ml DMF were added dropwise. After stirring for 1 hour at 0° C. and 1 hour at room temperature the mixture was concentrated under reduced pressure and purified by preparative HPLC (CH$_3$CN/H$_2$O gradient+0.1% TFA). 44 mg of racemic 3-((1R,3R)-3-tert-Butoxycarbonylamino-cyclopentyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid tert-butyl ester (20% yield) were obtained.

LC/MS (method B): R$_t$=1.10 min, m/z: 689.3 [MH$^+$].

F (S)-3-((1R,3R)-3-Amino-cyclopentyl)-2-[3-((9S, 12R)-9-isopropyl-11-oxo-2,7-dioxa-10-aza-bicyclo [12.2.2]octadeca-1(17),14(18),15-trien-12-yl)-ureido]-2-methyl-propionic acid (A compound of formula II)

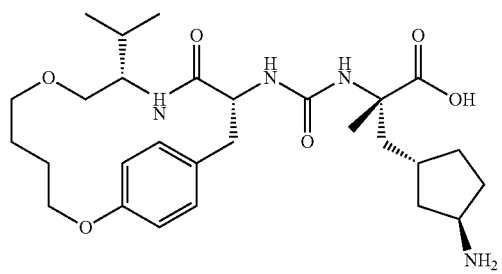 [SMILES: CC(C)[C@H]1COCCCCOc2ccc(cc2)C[C@@H](NC(=O)N[C@@](C)(C[C@@H]2CC[C@@H](N)C2)C(=O)O)C(=O)N1]

44 mg (63.1 µmol) of racemic 3-((1R,3R)-3-tert-butoxycarbonylamino-cyclopentyl)-2-[3-((9S,12R)-9-isopropyl-11-oxo-2,7-dioxa-10-aza-bicyclo[12.2.2]octadeca-1(17),14 (18),15-trien-12-yl)-ureido]-2-methyl-propionic acid tert-butyl ester (Compound of step E) were dissolved in a mixture of 0.5 ml TFA, 15 µl H$_2$O and 15 µl triisopropylsilane and stirred for 1 hour at room temperature. The mixture was purified by preparative RP-HPLC (CH$_3$CN/H$_2$O gradient+0.1% TFA) to give 32 mg pure racemic (S)-3-((1R,3R)-3-Amino-cyclopentyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid. The diastereomers were separated by using a chiral stationary phase (Chiralpak IC 250×20 mm) and a mixture of heptane/ethanol/methanol (5:1:1, conditioned with N,N-diethylamine) as mobile phase. Accordingly, 8.5 mg of pure (S)-3-((1R,3R)-3-Amino-cyclopentyl)-2-[3-((9S,12R)-9-isopropyl-11-oxo-2,7-dioxa-10-aza-bicyclo [12.2.2]octadeca-1(17),14(18),15-trien-12-yl)-ureido]-2-methyl-propionic acid were obtained as colorless amorphous material (25% yield).

LC/MS (method B): R$_t$=0.64 min, m/z: 533.3 [MH$^+$].

Example 4

(S)-3-(6-Amino-pyridin-3-yl)-2-[3-((3S,6R)-3-isopropyl-5-oxo-1,8-dioxa-4-aza-cyclododec-6-yl)-ureido]-2-methyl-propionic acid

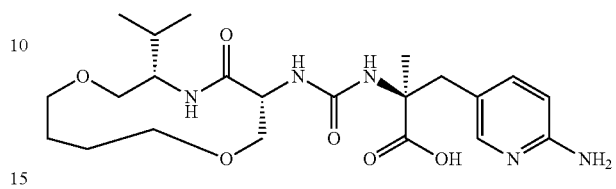

A. 2-(Benzhydrylidene-amino)-3-(6-tert-butoxycarbonylamino-pyridin-3-yl)-2-methyl-propionic acid tert-butyl ester ester (A compound of formula XI)

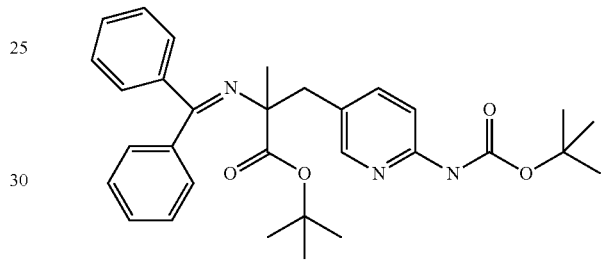

A solution of 3.35 g (10.83 mmol) (S)-2-(Benzhydrylidene-amino)-propionic acid tert-butyl ester (Compound from example 2, step A) in 25 mL DMF was cooled to 0° C. under Argon atmosphere, 8.13 mL NaHMDS (2M in THF, 16.25 mmol) were slowly added and the mixture was stirred for 30 min. A solution of 3.11 g (10.83 mmol) (5-Bromoethyl-pyridin-2-yl)-carbamic acid tert-butyl ester in 15 mL DMF was added dropwise and the mixture was allowed to warm to room temperature. After 5 hours the reaction was quenched with NH$_4$Cl-solution, ethyl acetate was added and the layers were separated. The organic layer was washed with NaCl-solution, dried and concentrated under reduced pressure. The residue was purified by flash chromatography on silica gel using n-heptane/ethyl acetate as an eluent to give 1.09 g (19% yield) of the title compound.

LC/MS (method B): R$_t$=1.01 min, m/z: 516.3 [MH$^+$].

B. 2-Amino-3-(6-tert-butoxycarbonylamino-pyridin-3-yl)-2-methyl-propionic acid tert-butyl ester ester (A compound of formula VIII)

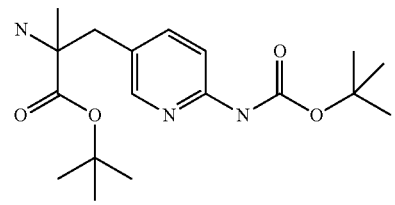 [SMILES: CC(C)(C)OC(=O)Nc1ccc(CC(C)(N)C(=O)OC(C)(C)C)cn1]

To a solution of 680 mg (1.32 mmol) 2-(Benzhydrylidene-amino)-3-(6-tert-butoxycarbonylamino-pyridin-3-yl)-2-methyl-propionic acid tert-butyl ester (Compound from step A) in 120 mL ethyl acetate were added 67 mg Pd/C (10%) and the mixture was hydrogenated at 2 bar H$_2$ at room temperature. After stirring overnight, 100 mL MeOH were added together with another portion of 67 mg 10% Pd/C and the was hydrogenation repeated. After one day, the catalyst was filtered off and the solution concentrated under reduced pressure. The residue was purified by prep. HPLC to give 358 mg (58% yield) of the desired compound.

LC/MS (method B): R$_t$=0.65 min, m/z: 352.3 [MH$^+$].

C. (S)-2-Amino-3-(6-tert-butoxycarbonylamino-pyridin-3-yl)-2-methyl-propionic acid tert-butyl ester (A compound of formula VIII)

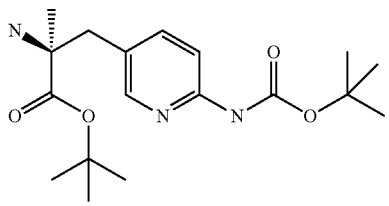 [SMILES: CC(C)(C)OC(=O)Nc1ccc(C[C@](C)(N)C(=O)OC(C)(C)C)cn1]

12.5 g of racemic 2-Amino-3-(6-tert-butoxycarbonylamino-pyridin-3-yl)-2-methyl-propionic acid tert-butyl ester were separated into its enantiomers using Chiralcel OD-H as a stationary phase and n-heptane/ethanol with 0.1% diethylamine as mobile phase to give 5.5 g (44% yield) of the desired material.

D. (S)-3-(6-tert-Butoxycarbonylamino-pyridin-3-yl)-2-[3-((3S,6R)-3-isopropyl-5-oxo-1,8-dioxa-4-aza-cyclododec-6-yl)-ureido]-2-methyl-propionic acid tert-butyl ester (A compound of formula XII)

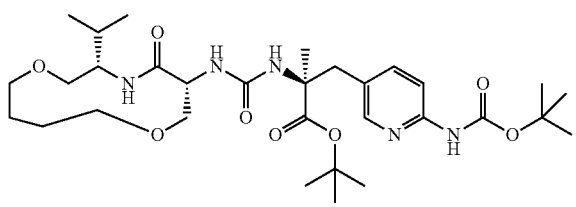 [SMILES: CC(C)[C@H]1COCCCCOC[C@@H](NC(=O)N[C@@](C)(Cc2ccc(NC(=O)OC(C)(C)C)nc2)C(=O)OC(C)(C)C)C(=O)N1]

0.358 g (1.018 mmol) (S)-2-Amino-3-(6-tert-butoxycarbonylamino-pyridin-3-yl)-2-methyl-propionic acid tert-butyl ester (Compound form step C) were added to a solution of 0.165 g (1.018 mmol) 1,1'-Carbonyldiimidazole in 16 mL DMF and stirred at RT under Argon. A solution of 0.481 g (1.018 mmol) (3R,6R)-6-Amino-3-isopropyl-1,8-dioxa-4-aza-cyclododecan-5-one-trifluoroacetate and 0.376 mL (2.036 mmol) N,N-diisopropyl ethyl amine in 16 mL DMF was added and stirred overnight at RT under Argon. The solvent was evaporated and the residue purified by prep. HPLC to yield 0.218 g (35% yield) of the desired product.

LC/MS (method B): R$_t$=0.84 min, m/z: 622.45 [MH$^+$].

E. (S)-3-(6-Amino-pyridin-3-yl)-2-[3-((3S,6R)-3-isopropyl-5-oxo-1,8-dioxa-4-aza-cyclododec-6-yl)-ureido]-2-methyl-propionic acid (A compound of formula II)

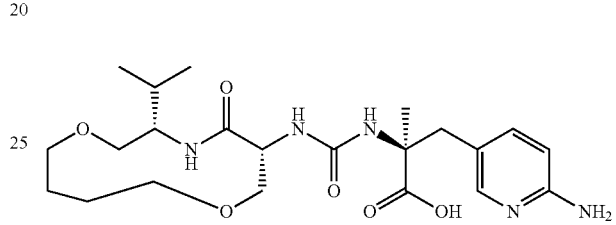

A solution of 0.218 g (0.3 mmol) (S)-3-(6-tert-Butoxy-carbonylamino-pyridin-3-yl)-2-[3-((3S,6R)-3-isopropyl-5-oxo-1,8-dioxa-4-aza-cyclododec-6-yl)-ureido]-2-methyl-propionic acid tert-butyl ester (Compound from step D) was dissolved in 6 mL DCM/TFA (1:1, v/v) and stirred for 3 hours at RT. Upon evaporation, the residue was taken up in 1N HCl and freeze dried to give 0.148 g of the title compound as hydrochloride salt (99% yield).

LC/MS (method C): R$_t$=0.73 min, m/z: 465.3 [MH$^+$]

$^1$H-NMR (DMSO-d6, 400 MHz) δ[ppm]=8.00 (2H, s, br), 7.70-7.58 (2H, m), 7.18 (d, 1H), 6.91 (d, 1H), 6.60-6.56 (m, 2H), 4.07 (t, 1H), 3.72-3.29 (m, 10H), 3.11 (dd, 2H), 1.78 (m, 1H), 1.67 (m, 2H), 1.51 (m, 1H), 1.28 (s, 3H), 0.86 (d, 3H), 0.80 (d, 3H).

The table below illustrates the chemical structures of some examples of the compounds of formula I according to the invention.

TABLE 1

| Example | Chemical name | Formula |
|---|---|---|
| 1 | (S)-3-(6-Amino-pyridin-3-yl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid | |

TABLE 1-continued

| Example | Chemical name | Formula |
|---|---|---|
| 2 | (S)-3-(3-Amino-cyclobutyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid | *(structure)* |
| 3 | (S)-3-((1R,3R)-3-Amino-cyclopentyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid | *(structure)* |
| 4 | (S)-3-(6-Amino-pyridin-3-yl)-2-[3-((3S,6R)-3-isopropyl-5-oxo-1,8-dioxa-4-aza-cyclododec-6-yl)-ureido]-2-methyl-propionic acid | *(structure)* |

Pharmacological Examples

Pharmacological Example 1

TAFIa Inhibition

The prepared substances were tested for TAFIa inhibition using the Actichrome plasma TAFI Activity Kit from American Diagnostica (Pr. No. 874). This entailed adding 28 μl of assay buffer (20 mM Hepes, 150 mM NaCl, pH 7.4) and 10 μl of TAFIa (American Diagnostica Pr. No. 874TAFIA; 2.5 μg/ml) to 2 μl of 2.5 mM DMSO solution of the substance and incubating in a 96 half-well microtiter plate at room temperature for 15 minutes. The enzyme reaction was started by adding 10 μl of TAFIa developer (prediluted 1:2 with assay buffer). The time course of the reaction was followed at 420 nm in a microtiter plate reader (SpectraMax plus 384; Molecular Devices) for 15 minutes.

The $IC_{50}$ values were calculated from the averaged values (duplicate determination) of serial dilutions of the substance with the aid of the Softmax Pro software (version 4.8; Molecular Devices).

TABLE 2

$IC_{50}$ values for the example compounds and comparision examples according to WO2009146802

| Example No. | $IC_{50}$ [μM] | $IC_{50}$ of Comparison examples [μM] | Structures of comparision examples |
|---|---|---|---|
| 1 | 0.0003 | 0.009 | *(structure)* (Example 5-2 of WO2009146802) |

TABLE 2-continued

IC$_{50}$ values for the example compounds and comparision examples according to WO2009146802

| Example No. | IC$_{50}$ [μM] | IC$_{50}$ of Comparison examples [μM] | Structures of comparision examples |
|---|---|---|---|
| 2 | 0.0003 | 0.004 | 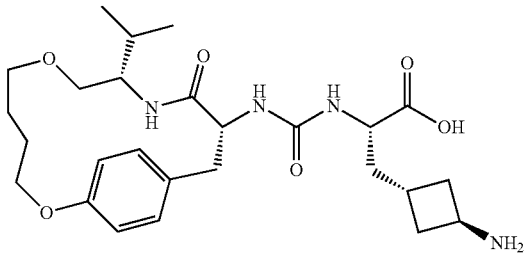 [SMILES: CC(C)[C@H]1COCCCCOc2ccc(cc2)C[C@@H](NC(=O)N[C@@H](C[C@H]2C[C@H](N)C2)C(=O)O)C(=O)N1] |
| 3 | 0.001 | — | — |
| 4 | 0.001 | 0.055 | 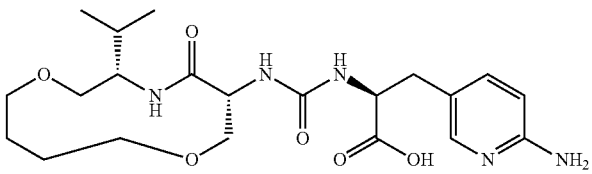 [SMILES: CC(C)[C@H]1COCCCCOC[C@@H](NC(=O)N[C@@H](Cc2ccc(N)nc2)C(=O)O)C(=O)N1] |

The comparison examples can be prepared as described in WO2009146802 or via similar processes.

It is apparent that the compounds of formula I according to the invention have a strong inhibitory activity for the enzyme TAFIa. Additionally, table 2 shows that the compounds of formula I according to the invention show surprisingly a significantly higher activity as TAFIa inhibitors than the compounds described in WO2009146802.

Furthermore, it was surprisingly found that compounds of formula I show in contrast to TAFIa inhibitors described in WO2009146802 a time dependent IC$_{50}$ and therefore a slow tight-binding mechanism (longer residence time) which can result in a favourable longer duration of action. Pharmacological example 2 and Table 3 exemplify this observation.

Pharmacological Example 2

TAFIa Inhibition at Variable Perincubation Times

The prepared substances were tested for TAFIa inhibition using the Actichrome plasma TAFI Activity Kit from American Diagnostica (Pr. No. 874). This entailed adding 28 μl of assay buffer (20 mM Hepes, 150 mM NaCl, pH 7.4) and 10 μl of TAFIa (American Diagnostica Pr. No. 874TAFIA; 2.5 μg/ml) to 2 μl of 2.5 mM DMSO solution of the substance and incubating in a 96 half-well microtiter plate at room temperature for variable pre-incubation times (0, 5, 15 and 30 minutes). The enzyme reaction was started by adding 10 μl of TAFIa developer (prediluted 1:2 with assay buffer). The time course of the reaction was followed at 420 nm in a microtiter plate reader (SpectraMax plus 384; Molecular Devices) for 15 minutes.

The IC$_{50}$ values were calculated from the averaged values (duplicate determination) of serial dilutions of the substance with the aid of the Softmax Pro software (version 4.8; Molecular Devices). The coefficient of IC$_{50}$ values was determined by IC$_{50}$ value at 0 min over IC$_{50}$ value at x minutes, wherein x can be 0, 5, 15 or 30 minutes of pre-incubation time.

TABLE 3

Coefficient of IC$_{50}$s (IC$_{50}$ value at 0 min/IC$_{50}$ value at x min preincubation time) for example 2 and its comparison example from WO2009146802.

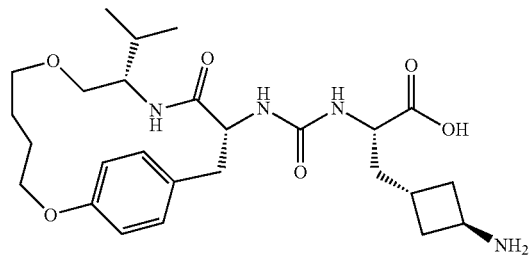 [SMILES: CC(C)[C@H]1COCCCCOc2ccc(cc2)C[C@@H](NC(=O)N[C@@H](C[C@H]2C[C@H](N)C2)C(=O)O)C(=O)N1]

| Pre-incubation time [min] | Example 2 Coefficient | Coefficient |
|---|---|---|
| 0 | 1 | 1 |
| 5 | 2.9 | 0.5 |
| 15 | 5.8 | 1.3 |
| 30 | 7.7 | 1 |

At the pre-incubation time of 0 minutes the coefficient for example 2 and the comparison compound according to WO1009146802 are similar. With increasing pre-incubation time the two compounds show a different behaviour. For compound 2 the coefficient increases. For the comparison compound the coefficient stays nearly constant in time. This shows the time dependent inhibitor activity of the compounds of formula I in contrast to the compounds according to WO1009146802 and therefore a slow tight-binding mechanism (longer residence time) which can result in a favourable longer duration of action of the compounds according to the invention.

The compounds of according to the invention can therefore be used as medicaments, especially medicaments which are inhibitors of TAFIa.

Accordingly, in another of its aspects, the invention provides medicaments which comprise a compound of formula (I), in any of its stereoisomeric forms or a mixture of stereoisomeric forms in any ratio, or a pharmaceutically acceptable salt thereof.

The present invention further provides a compound of the formula I, in any of its stereoisomeric forms or a mixture of stereoisomeric forms in any ratio, or a pharmaceutically acceptable salt thereof for use in the treatment of one or more disorders which are associated with thromboses, embolisms, hypercoagulability or fibrotic changes, more specifically of one or more disorders from the series of myocardial infarction, angina pectoris and other forms of acute coronary syndrome, stroke, peripheral vascular disorders, deep vein thrombosis, pulmonary embolism, embolic or thrombotic events caused by cardiac arrhythmias, cardiovascular events such as restenosis following revascularization and angioplasty and similar procedures such as stent implantations and bypass operations, or reducing the risk of thrombosis following surgical procedures such as operations on the knee and hip joints, or in the context of disseminated intravascular coagulation, sepsis, intravascular events associated with fibrin formation, atherosclerosis, diabetes and the metabolic syndrome and the sequelae thereof, tumor growth and tumor metastasis, inflammatory and degenerative articular disorders such as rheumatoid arthritis and osteoarthritis, impairments of the hemostatic system such as fibrin deposits, fibrotic changes of the lung such as chronic obstructive pulmonary disease, adult respiratory distress syndrome or fibrin deposits in the eye following eye operations or scarring.

The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence.

The present invention, according to another of its aspects, also provides a method of treatment of the disorders indicated above, which comprises administering to a patient an effective dose of compound of formula (I) according to the invention, in any of its stereoisomeric forms or a mixture of stereoisomeric forms in any ratio, or a pharmaceutically acceptable salt thereof.

The compounds according to the invention can therefore be used for preparing medicaments, especially medicaments which are inhibitors of TAFIa.

According to another of its aspects, the present invention relates to pharmaceutical compositions comprising as active principle a compound according to the invention. These pharmaceutical compositions comprise an effective dose of at least one compound according to the invention in any of its stereoisomeric forms or a mixture of stereoisomeric forms in any ratio, or a pharmaceutically acceptable salt thereof and also at least one pharmaceutically acceptable excipient.

The compounds of the formula I and their pharmaceutically acceptable salts, and pharmaceutical compositions and medicaments comprising them, can be administered enterally, for example by oral or rectal administration, parenterally, for example by intravenous, intramuscular or subcutaneous injection or infusion, or by another type of administration such as topical, percutaneous, transcutaneous, nasal, pharyngal or inhalative administration, the preferred form of administration depending on the particulars of the specific case. The compounds of the formula I and their pharmaceutically acceptable salts can also be used in combination with other pharmaceutically active compounds.

The pharmaceutical compositions and medicaments according to the invention normally contain from about 0.01 to about 90 percent by weight of a compound or compounds of the formula I or pharmaceutically acceptable salt thereof, and an amount of active ingredient of the formula I and/or its pharmaceutically acceptable salt which in general is from about 0.01 mg to about 1 g, in particular from about 0.2 mg to about 500 mg, for example from about 1 mg to about 300 mg, per dose unit. Depending on the kind of the pharmaceutical composition and other particulars of the specific case, the amount may deviate from the indicated ones. The production of the pharmaceutical compositions and medicaments can be carried out in a manner known per se and familiar to the person skilled in the art. For this, the compounds of the formula I and/or their pharmaceutically acceptable salts can be mixed together with one or more solid or liquid vehicles and/or excipients, if desired also in combination with one or more other pharmaceutically active compounds, and brought into a suitable form for dosage and administration, which can then be used in human medicine or veterinary medicine. In the production of solid pharmaceutical compositions, for example, dry granules or wet granules can be prepared. The compounds of the formula I and their pharmaceutically acceptable salts can also be lyophilized and the resulting lyophilizates be used, for example for producing medicaments for injection or infusion.

As vehicles, which may also be looked upon as diluents or solvents or bulking agents, and excipients suitable organic and inorganic substances can be used which do not react in an undesired manner with the compounds of the formula I. As examples of types of excipients, or additives, which can be contained in the pharmaceutical compositions and medicaments, lubricants, preservatives, gel formers, solubilizers, thickeners, stabilizers, disintegrants, wetting agents, emulsifiers, dispersants, antifoaming agents, salts, buffer substances, colorants, flavorings, antioxidants or agents for achieving a depot effect may be mentioned. The said vehicles, excipients or additives are selected, in accordance with the pharmaceutical form and method of administration desired, from the customary excipients, which are known to a person skilled in the art.

For oral and rectal use, pharmaceutical forms such as, for example, tablets, coated tablets, sugar-coated tablets, granules, hard and soft gelatin capsules, suppositories, solutions, including oily, alcoholic or aqueous solutions, or drops, furthermore suspensions or emulsions, can be used. For parenteral use, for example by injection or infusion, pharmaceutical forms such as solutions, suspensions or emulsions, for example aqueous solutions, can be used. For topical use, pharmaceutical forms such as ointments, creams, pastes, lotions, gels, sprays, foams, aerosols, solutions or powders can be used. Suitable as pharmaceutical compositions for administration in the form of aerosols or sprays are, for example, solutions, suspensions or emulsions of the active ingredient of the formula I or its pharmaceutically acceptable salt in a pharmaceutically acceptable solvent, such as ethanol or water or a mixture of such solvents, wherein the formulation may also comprise other pharmaceutical excipients such as surfactants, emulsifiers and stabilizers, and a propellant gas. Such a composition comprises the active ingredient normally in a concentration of about 0.01 percent to about 10 percent, in particular of about 0.3 percent to about 3 percent, by weight.

As usual, the dosage of the compounds of the formula I and the frequency of administration depend on the circumstances of the specific case and are adjusted by the physician according to the customary rules and procedures. They depend, for example, on the compound of the formula I administered and its potency and duration of action, on the nature and severity of the individual syndrome, on the gender, age, weight and the individual responsiveness of the human or animal to be treated, on whether the treatment is acute or chronic or prophylactic, or on whether further pharmaceutically active compounds are administered in addition to a compound of the formula I. Normally, in the case of administration to an adult weighing about 75 kg, a dose from about 0.00013 mg to about 10 mg per kg per day, in particular from about 0.001 mg to about 5 mg per kg per day (in each case in mg per kg of body weight), is sufficient. The daily dose can be administered in the form of a single dose or divided into a number of individual doses, for example two, three or four individual doses. The administration can also be carried out continuously, for example by continuous injection or infusion. Depending on the individual behavior in a specific case, it may be necessary to deviate upward or downward from the indicated dosages, for example in acute episodes of a disease or in an intensive care unit.

The TAFIa inhibitors according to the invention can be administered both as monotherapy and in combination or together with all antithrombotics (anticoagulants and platelet aggregation inhibitors), thrombolytics (plasminogen activators of every type, for example tissue-type plasminogen activator (t-PA)), or other substances having profibrinolytic activity, antihypertensives, regulators of blood glucose, lipid-lowering agents and antiarrhythmics.

What is claimed:
1. A compound of the formula I,

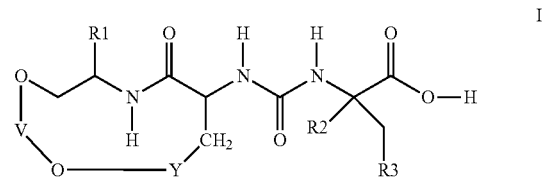

in any of its stereoisomeric forms or a mixture of stereoisomeric forms in any ratio, or a pharmaceutically acceptable salt thereof,
wherein
V is —(CH$_2$)$_4$;
Y is a covalent bond or phenyl, optionally substituted by one, two or three R15 groups;
R1 is —(C$_1$-C$_6$)-alkyl
R2 is methyl;
R3 is Het substituted by —NH$_2$, or (C$_4$-C$_8$)-cycloalkyl substituted by —NH$_2$,
wherein Het is selected from pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophenyl, bonded via a ring carbon atom to the methylene group to which R3 is attached, and
wherein Het and —(C$_4$-C$_8$)-cycloalkyl are optionally substituted by one, two or three R15 groups; and
each R15 group is independently —(C$_1$-C$_4$)-alkyl, —O—CF$_3$, —NH$_2$, —OH, —CF$_3$ or halogen.

2. The compound of claim 1, in any of its stereoisomeric forms or a mixture of stereoisomeric forms in any ratio, or a pharmaceutically acceptable salt thereof, wherein
V is —(CH$_2$)$_4$;
Y is a covalent bond or phenyl;
R1 is isopropyl;
R2 is methyl; and R3 is Het substituted by —NH$_2$, or —(C$_4$-C$_8$)-cycloalkyl substituted by —NH$_2$,
wherein Het is selected from pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophenyl, bonded via a ring carbon atom to the methylene group to which R3 is attached.

3. The compound of claim 1, in any of its stereoisomeric forms or a mixture of stereoisomeric forms in any ratio, or a pharmaceutically acceptable salt thereof, wherein
V is —(CH$_2$)$_4$—;
Y is a covalent bond or phenyl;
R1 is isopropyl;
R2 is methyl; and
R3 is pyridinyl substituted by —NH$_2$, cyclobutyl substituted by —NH$_2$, or cyclopentyl substituted by —NH$_2$.

4. The compound of claim 1 having the structure of formula II,

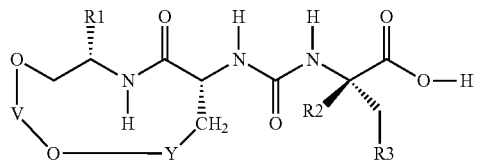

in any of its stereoisomeric forms or a mixture of stereoisomeric forms in any ratio, or a pharmaceutically acceptable salt thereof.

5. The compound of claim 1, or a pharmaceutically acceptable salt thereof, wherein the compound is:
(S)-3-(6-Amino-pyridin-3-yl)-2-[3-((9 S,12R)-9-isopropyl-11-oxo-2,7-dioxa-10-aza-bicyclo[12.2.2]octadeca-1(17),14(18),15-trien-12-yl)-ureido]-2-methyl-propionic acid;
(S)-3-(3-Amino-cyclobutyl)-2-[3-((9S,12R)-9-isopropyl-11-oxo-2,7-dioxa-10-aza bicyclo[12.2.2]octadeca-1(17),14(18),15-trien-12-yl)-ureido]-2-methyl-propionic acid;
(S)-3-((1R,3R)-3-Amino-cyclopentyl)-2-[3-((9S,12R)-9-isopropyl-11-oxo-2,7-dioxa-10-aza-bicyclo[12.2.2]octadeca-1(17),14(18),15-trien-12-yl)-ureido]-2-methyl-propionic acid; or
(S)-3-(6-Amino-pyridin-3-yl)-2-[3-((3 S,6R)-3-isopropyl-5-oxo-1,8-dioxa-4-aza-cyclododec-6-yl)-ureido]-2-methyl-propionic acid.

6. A pharmaceutical composition, comprising a compound of claim 1, in any of its stereoisomeric forms or a mixture of stereoisomeric forms in any ratio, or a pharmaceutically acceptable salt thereof, and a pharmaceutically acceptable carrier.

7. A method for preparing a compound of claim 1, the method comprising:
reacting a compound of formula XVI:

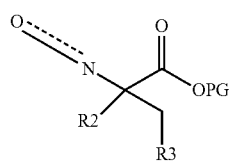

with a compound of formula VII:

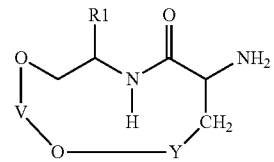

to provide a compound of claim 1,
wherein
V is —(CH$_2$)$_4$—;
Y is a covalent bond or phenyl, optionally substituted by one, two or three R15 groups;
R1 is —(C$_1$-C$_6$)-alkyl;
R2 is methyl;
R3 is Het substituted by —NH$_2$, or —(C$_4$-C$_8$)-cycloalkyl substituted by —NH$_2$,
wherein Het is selected from pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophenyl, wherein each group is bonded via a ring carbon atom to the methylene group to which R3 is attached, and
wherein Het and —(C$_4$-C$_8$)-cycloalkyl are optionally substituted by one, two or three R15 groups;
each R15 group is independently —(C$_1$-C$_4$)alkyl, —OCF$_3$, —NH$_2$, —OH, —CF$_3$ or halogen; and
PG is an ester protective group.

8. The method of claim 7, further comprising preparing the compound of formula XVI:

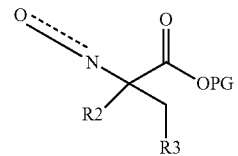

the method comprising:
reacting a compound of formula XV:

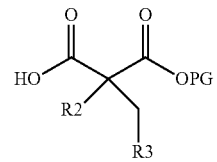

with an azide source to provide a compound of formula XVI,
wherein
R2 is methyl;
R3 is Het substituted by —NH$_2$, or —(C$_4$-C$_8$)-cycloalkyl substituted by —NH$_2$,
wherein Het is selected from pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophenyl, wherein each group is bonded via a ring carbon atom to the methylene group to which R3 is attached, and wherein Het and —($C_4$-$C_8$)-cycloalkyl are optionally substituted by one, two or three R15 groups;
each R15 group is independently —($C_1$-$C_4$)alkyl, —$OCF_3$, —$NH_2$, —OH, —$CF_3$ or halogen; and
PG is an ester protective group.

9. A pharmaceutical composition comprising a compound of claim 1 and an antithrombotic, thrombolytic or other substance having profibrinolytic activity.

* * * * *